(12) United States Patent
Akervall et al.

(10) Patent No.: US 9,302,063 B2
(45) Date of Patent: Apr. 5, 2016

(54) DENTAL APPLIANCE AND METHOD OF PROTECTING DENTITIONS DURING A TRANSORAL PROCEDURE WITH THE APPLIANCE

(71) Applicant: Akervall Technologies, Inc., Ann Arbor, MI (US)

(72) Inventors: Jan Akervall, Ann Arbor, MI (US); Valarie Thomas, Ann Arbor, MI (US); Johann Walter Schwank, Ann Arbor, MI (US)

(73) Assignee: Akervall Technologies, Inc., Ann Arbor, MI (US)

( * ) Notice: Subject to any disclaimer, the term of this patent is extended or adjusted under 35 U.S.C. 154(b) by 4 days.

(21) Appl. No.: 14/602,546

(22) Filed: Jan. 22, 2015

(65) Prior Publication Data
US 2016/0001027 A1     Jan. 7, 2016

Related U.S. Application Data

(60) Provisional application No. 62/019,456, filed on Jul. 1, 2014.

(51) Int. Cl.
*A61M 16/04*     (2006.01)
*A61B 1/267*     (2006.01)

(52) U.S. Cl.
CPC .............. *A61M 16/049* (2014.02); *A61B 1/267* (2013.01)

(58) Field of Classification Search
CPC .................................................... A61M 16/049
See application file for complete search history.

(56) References Cited

U.S. PATENT DOCUMENTS 3,112,744 A * 12/1963 Grossberg ..................... 128/862
4,112,934 A     9/1978 Rizk
(Continued)

FOREIGN PATENT DOCUMENTS

WO     2013096466 A1     6/2013

OTHER PUBLICATIONS

Enrico Monaca, MD; Norbert Fock, MD; Manfred Doehn, MD; Frank Wappler, MD, The Effectiveness of Preformed Tooth Protectors During Endotracheal Intubation: An UpperJaw Model; vol. 105, No. 5, Nov. 2007; International Anesthesia Research Society; Koln, Germany.
(Continued)

*Primary Examiner* — Victoria J Hicks
*Assistant Examiner* — Tarla Patel
(74) *Attorney, Agent, or Firm* — Marshall & Melhorn, LLC

(57) ABSTRACT

A dental appliance for protecting teeth has two front flaps separated by a forward cusp, and two side flaps separated from the forward front flaps by side cusps. An open area is provided in each of the forward front flaps. The appliance may also have a rear palate portion with a rear cusp. The appliance may have a line of symmetry that extends from the forward cusp to the rear cusp. Open spaces may be distributed throughout the sheet of material.

A method of protecting the dentition of a patient during a transoral procedure or intubation includes the steps of providing the appliance in a planar first state and placing the appliance in the mouth of a patient so the patient's dentition crowns are located along a bite line on the appliance. The method also includes molding the appliance into a second, non-planar state to conform to the patient's dentition and palate so that the dentition are protected during the transoral procedure or intubation.

23 Claims, 5 Drawing Sheets

(56) References Cited

U.S. PATENT DOCUMENTS

| | | | |
|---|---|---|---|
| 4,640,273 A | | 2/1987 | Greene et al. |
| 2002/0144687 A1 | | 10/2002 | Kittelsen et al. |
| 2007/0148612 A1 | * | 6/2007 | Massad ........................... 433/37 |
| 2007/0235040 A1 | | 10/2007 | Salcedo et al. |
| 2008/0156331 A1 | | 7/2008 | Isenberg et al. |
| 2009/0038624 A1 | * | 2/2009 | Akervall et al. ............. 128/861 |
| 2009/0117514 A1 | * | 5/2009 | Massad ........................... 433/39 |
| 2011/0220124 A1 | | 9/2011 | Vaska et al. |
| 2012/0325225 A1 | * | 12/2012 | Small ........................... 128/862 |

OTHER PUBLICATIONS

Ruben A. Lee, BE; Andre A. J. Van Zundert, PhD, MD, FRCA; Ralph L. J. G. Maassen, MD; Remi J. Willems, MD; Leon P. Beeke, BSC; Jan N. Schaaper, BSC; Johan Van Dobbelsteen, PhD; Peter A. Wieringa, PhD; Forces Applied to the Maxillary Incisors During Video-Assisted Intubation; vol. 108, No. 1, Jan. 2009; International Anesthesia Research Society; Eindhoven, The Netherlands.

Ueda N; Kirita T; Imai Y; Inagake K; Matsusue Y; Inoue S; Kawaguchi M; Furuya H; Dental Injury Associated with General Anesthesia and the Preventive Measures; Masui, May 2010; 59(5): 597-603.

U. Aromaa; P. Pesonen; K. Linko; T. Tammisto; Difficulties with Tooth Protectors in Endotracheal Intubation; Acta Anaesthesiol Scand 1988: 32: 304-307; Helsinki, Finland.

J. Mourao, J. Neto, C. Luis, C. Moreno, J. Barbosa, J. Carvalho and J. Tavares, Dental Injury After Conventional Direct Laryngoscopy: A Prospective Observational Study; Anaesthesia 2013, 68, 1059-1065; 2013 The Association of Anaesthetists of Great Britain and Ireland.

Navot Givol, Yael Gershtansky, Talia Halamish-Shani, Shlomo Taicher, Azriel Perel, Eran Segal; Perianesthetic Dental Injuries: Analysis of Incident Reports; Journal of Clinical Anesthesia 16: 173-176, 2004; Elsevier Inc., New York.

Myrna C. Newland MD, Sheila J. Ellis, K. Reed Peters, Jean A. Simonson, Timothy M. Durham, Fred A. Ullrich, John H. Tinker; Dental Injury Associated with Anesthesia: A Report of 161,687 Anesthetics Given Over 14 Years; Journal of Clinical Anesthesia 2007; 19, 339-345.

Jeremy Windsor, Jane Lockie; Anaesthesia and Dental Trauma; Anaesthesia and Intensive Care Medicine (Dental/Maxillofacial); 2008 Elsevier.

Jaemin Lee, John H. Choi, Yoon K.Lee, Eun S. Kim, Ou K. Kwon, Randolph H. Hastings; The Callander Laryngoscope Blade Modification is Associated with a Decreased Risk of Dental Contact; Can J. Anesth 2004; 51:2; 181-184.

Garth T. Olson, Edwin H. Moreano, Michael R. Arcuri, Henry T. Hoffman; Dental Protection During Rigid Endoscopy; Laryngoscope 105; Jun. 1995; 662-663.

Mark Domanski, Patty Lee, Nader Sadeghi; Cost-Effective Dental Protection During Rigid Endoscopy; Laryngoscope 121: Dec. 2011; 2590-91.

Henry Hoffman, Semirra Bayan, Josh Tokita, Douglas Van Daele, Robert Schneider; In Reference to Cost-Effective Dental Protection During Rigid Endoscopy; Laryngoscope 122; Oct. 2012; 2362.

International Search Report with Written Opinion for PCT/US2015/013471.

* cited by examiner

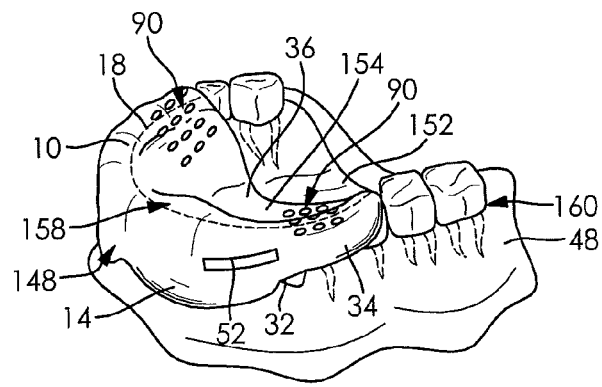
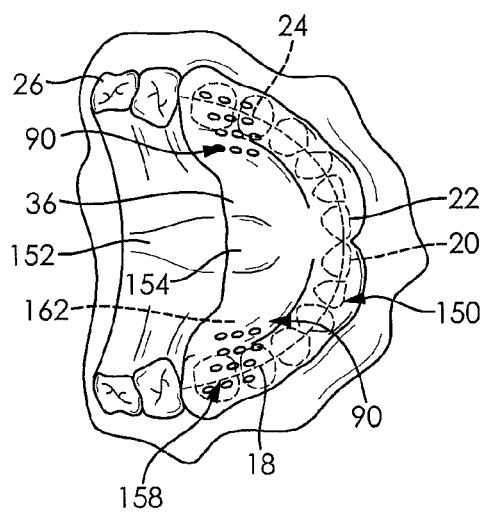
FIG. 2C
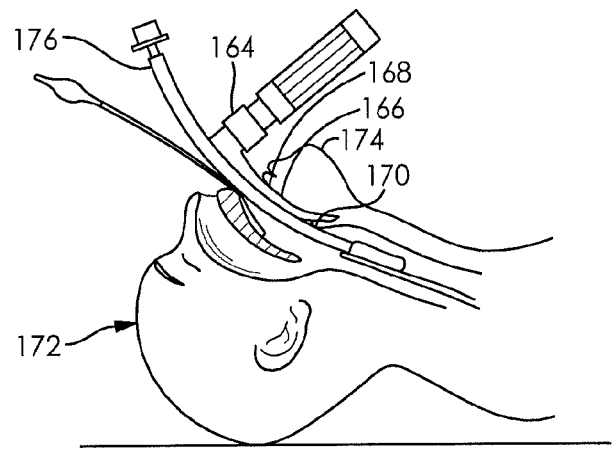
FIG. 3
FIG. 2D

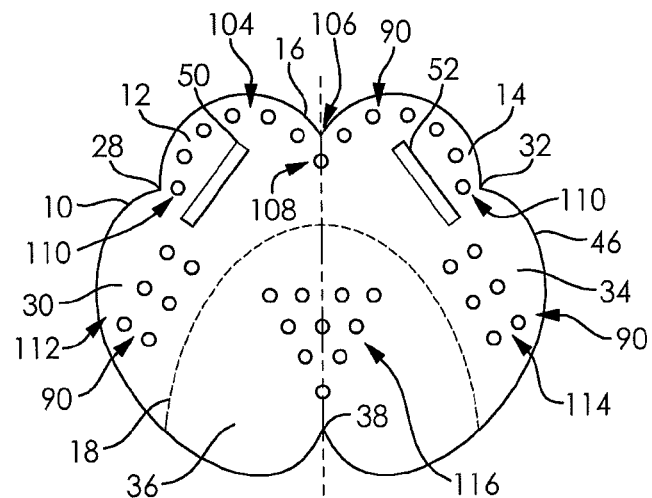

DENTAL APPLIANCE AND METHOD OF PROTECTING DENTITIONS DURING A TRANSORAL PROCEDURE WITH THE APPLIANCE

RELATED APPLICATIONS

This application claims priority to and the benefit of U.S. Provisional Application Ser. No. 62/019,456 filed on Jul. 1, 2014, which is incorporated by reference herein.

FIELD OF THE INVENTION

A dental appliance and a method of protecting dentition with the appliance during a transoral procedure are described.

BACKGROUND OF THE INVENTION

A relatively large number of patients are suffering dental injuries during transoral medical procedures. By way of example, a transoral procedure may be such as, but not limited to, an intubation or a rigid or flexible endoscopic procedure. During an intubation, an intubation laryngoscope 164, consisting of a curved, or straight, blade 166 is inserted into a patient's mouth 168 and throat 170 to examine the larynx, or for inserting a tube through it, as shown in FIG. 3. The patient 172 is in a supine position and is given induction anesthesia and muscle relaxants to facilitate the procedure. An anesthesiologist places the blade 166 deep on the patient's tongue, after which the lower jaw 174 is lifted to get full visualization of the voice box and the trachea, into which an endo-tracheal tube 176 may be inserted. During this process, the intubation laryngoscope 164 may need to be tilted for optimal visualization, thus applying pressure to the front teeth of the upper jaw (maxilla). This procedure is generally depicted in FIG. 3.

The applied pressure causes the central incisor teeth to become loaded with several Newtons (N) of force, sometimes as high as 87 N. It comes as no surprise then that studies have found the most frequently damaged teeth during an intubation are the central incisor teeth. Given the variability in both the state of healthiness of the dentition of a given patient undergoing an intubation procedure and the magnitude of force applied to achieve medical instrument entry to the trachea, a range of damage can occur to one or more teeth. Below is a chart briefly describing the damage ranges by class and description.

| Damage Ranges | |
|---|---|
| Class | Description |
| I | Fracture into the enamel layer |
| II | Fracture into the dentinal layer |
| III | Fracture into the pulp of the tooth |
| IV | Fracture of the root of the tooth |
| V | Subluxation of a tooth (a partial dislocation) |
| VI | Avulsion of a tooth (a tearing away of a body part accidently or surgically) |

Prior art dental appliances exist to protect the dentition of a patient during transoral medical procedures from damage or injury. Yet, dental injuries are reported in about 1.5% of intubations and are the major reason for law suits against anesthesiologists. Despite availability to such appliances, anesthesiologists and nurses, MDA's and CRNA's, respectively, tend not to use them for two major reasons: Firstly, a major disadvantage with existing dental appliances is that they fit extremely poorly onto the dentition. As a result of poor fit, the prior art appliances rarely remain in place on the dentition, and often become dislodged from the dentition during a transoral procedure or intubation. If the appliance is not in the proper position on the dentition, it can obstruct the view of the voice box thereby making it difficult to safely guide an endotracheal tube into the patient's larynx and further down into the trachea. Of course, if the appliance also does not remain in place, it will not protect the dentition. Intubation is not the only transoral procedure in which a patient's dentition is at risk for damage. Ear, nose and throat physicians, gastroenterologists and thoracic surgeons often use specialized instruments, such as a rigid laryngoscope, esophagoscope, or bronchoscope, during transoral procedures during which they apply pressure on the dentition and can cause damage as well.

Secondly, these prior art appliances are typically made of a soft, highly compressible polymer that often breaks down under pressure by undergoing extensive plastic deformation and even fracture, and therefore do not protect the dentition very well. The typical thermoplastic polymeric material used to construct these prior art appliances is ethylene vinyl acetate (EVA) which is well known to be a mechanically soft material. An indirect assessment of mechanical softness/hardness of a material is given by the basic material property, the Young's Modulus. A typical EVA (30% vinyl acetate) polymer often used to construct a prior art appliance has a Young's Modulus of 0.015 GPa. In contrast, the preferred polymer for construction of the subject invention appliance is polycaprolactone (PCL) which has a Young's Modulus that is two orders of magnitude greater at 1.2 GPa. The much greater Young's Modulus indicates a much stiffer material, essentially a harder material.

A comparatively much lower Young's Modulus also indicates a lesser capability to absorb and distribute force over an area. By definition the Young's Modulus is the ratio of the stress (force per unit area) applied in the axial direction to the strain, or deformation, incurred in that direction. The higher Young's Modulus of 1.2 GPa for PCL clearly indicates that the PCL material can absorb and distribute on the order of 100 times more force over the equivalent area than the EVA material, and this is before the onset of permanent material damage. Intuitively, the better dental protecting appliance is certainly the one that has a greater capacity to absorb force over an area, i.e. the dentition, in both the horizontal and axial directions.

Examples of appliances intended for the protection of teeth during transoral procedures or intubation include U.S. Pat. Nos. 4,112,934, 4,640,273, U.S. Patent Application Publication 2007/0235040, and U.S. Patent Application Publication 2008/0156331.

In view of the disadvantages of the prior art appliances, it would be desirable for a dental appliance to stay in place during any transoral procedure or intubation, to permit a clear view of the larynx and the tracheal inlet and to significantly diminish and/or re-direct forces applied to the dentition to prevent dental damage.

SUMMARY

In one embodiment, a sheet of material has two front flaps separated by a forward cusp, and two side flaps separated from the forward front flaps by side cusps. An open area is provided in each of the forward front flaps. A rear palate portion comprises two rear flaps. The rear flaps are separated by a rear cusp. The sheet may have a line of symmetry that extends from the forward cusp to the rear cusp. Open spaces may be distributed throughout the sheet of material.

In another embodiment, a method of protecting the dentition of a patient during a transoral procedure or intubation is described. The method includes the steps of providing the appliance in a planar first state and placing the appliance in the mouth of a patient so the patient's dentition crowns are located along a bite line on the appliance. The method also includes molding the appliance into a second, non-planar state to conform to the patient's dentition and palate. The method further includes dissipating a force applied to the dentition through the appliance at least through the use of the above-mentioned open areas and open spaces.

BRIEF DESCRIPTION OF THE DRAWINGS

The features of the subject will be better understood in the context of the detailed description in conjunction with the drawings in which:

FIG. 2C is a rear perspective view of the appliance of FIG. 1 on the dentition of a patient;

FIG. 2D is a plan view of the appliance of FIG. 1 on the dentition of a patient;

FIG. 3 is a partial cut-away side view of a medical instrument (laryngoscope) and intubation tubes inserted into the oral cavity of a patient in contact with the maxillary central incisor teeth;

FIG. 4D is a top view of another embodiment of an appliance in a first, planar state;

FIG. 4E is a top view of another embodiment of an appliance in a first, planar state;

FIG. 4F is a top view of another embodiment of an appliance in a first, planar state;

DETAILED DESCRIPTION

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1A:
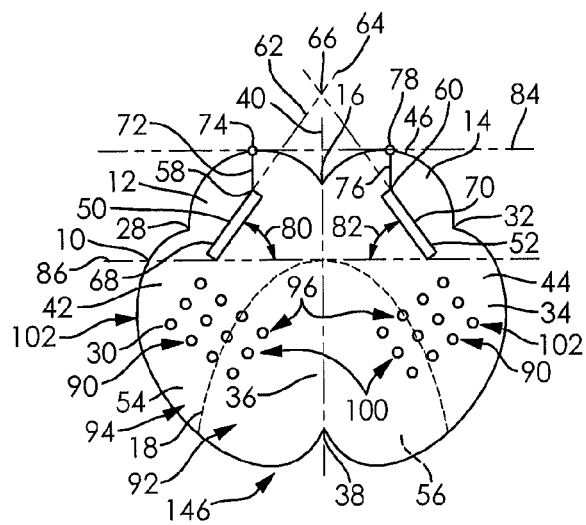
FIG. 1A is a top view of one embodiment of an appliance in a first, planar state.

Turning now to FIG. 1A, one embodiment of a dental appliance 10 is depicted. A preferred embodiment of the dental appliance 10 is shown in a flattened, first state. The appliance 10 is a one-piece, unitary and integrally formed sheet of material. In one embodiment, the appliance 10 may be 1 mm to 2 mm thick and fabricated from a polycaprolactone thermoplastic material. Such a material is widely available, inexpensive and readily disposable when the appliance 10 is exhausted.

The appliance 10 comprises a first front flap 12 and a second front flap 14, which together are called a maxillary flap. A forward cusp 16 is located between the two flaps 12, 14. The cusp 16 extends inwardly into the appliance 10 at least partially dividing the first front flap 12 and the second front flap 14. The cusp 16 extends inwardly toward, but preferably does not reach, a bite line 18.

Figure 2A:
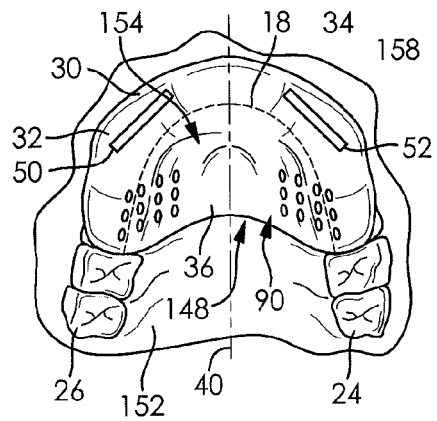
FIG. 2A is a perspective view of the appliance of FIG. 1 on the dentition of a patient.

The bite line 18 is the line on the appliance 10 along which the incisal edges 20 of the incisors 22 and the tips of the occluding surfaces 24 of the posterior teeth 26 come in contact with the appliance 10, as shown in FIG. 2D. Together, these edges 20 and surfaces 24 are called crowns herein. The bite line 18 is generally arch-shaped to be complementary to the arrangement of teeth in a patient's mouth.

A first side cusp 28 further defines the first front flap 12. The first side cusp 28 is located between the first front flap 12 and a first side flap 30. The first side cusp 28 extends inwardly into the appliance 10 toward the bite line 18. The first side cusp 28 may extend inwardly into the appliance 10 at the same depth as the forward cusp 16 or to a greater or lesser extent.

A second side cusp 32 further defines the second front flap 14. The second side cusp 32 is located between the second front flap 14 and a second side flap 34. The second side cusp 32 extends inwardly into the appliance 10 toward the bite line 18. The second side cusp 32 may extend inwardly into the appliance 10 at the same depth as the forward cusp 16 or to a greater or lesser extent.

The first and second side flaps 30, 34 extend to, and are part of, a rear palate portion 36. The flaps 30, 34 meet together at a rear cusp 38. The rear cusp 38 extends inwardly into the rear palate portion 36 to divide the flaps 30, 34. The rear cusp 38 may extend inwardly into the appliance 10 at the same depth as the forward cusp 16 and/or the side cusps 28, 32 or to a greater or lesser extent. In the first state, the rear palate portion 36 is a planar area located behind the bite line 18. A line of symmetry 40 for the appliance 10 bisects the rear palate portion 36.

In the embodiment depicted in FIG. 1A, the line of symmetry 40 extends from the forward cusp 16 to the rear cusp 38. The line of symmetry 40 equally divides the appliance 10 into a first half 42 and a second half 44, which are symmetric with one another. More particularly, the line of symmetry 40 results in a mirror image between the first half 42 and the second half 44. It is permissible, however, for the first half 42 to be non-symmetrical with the second half 44.

A perimeter 46 defines the first front flap 12, the second front flap 14, and the side flaps 30, 34. The perimeter is preferably rounded, or curvilinear. This embodiment is envisioned to impose the least, if any, discomfort to the wearer of the dental appliance 10 since it has no sharp corners or edges to embed into the soft gum tissue 48.

As shown in FIG. 1A, the appliance 10 has first and second open areas 50, 52 in the first front and second front flap 12, 14, respectively. In this embodiment, both open areas 50, 52, which may be a slot, have a rectangular shape. The open areas 50, 52 extend through the appliance 10 from a first planar side 54 to a second planar side 56. The second planar side 56 is opposite the first planar side 54. The second planar side 56 may be parallel to the first planar side 54.

The first open area has a first corner 58 adjacent the forward cusp 16. The second open area 52 also has a first corner 60 adjacent the forward cusp 16. The first and second open areas 50, 52 are angled so that first and second lines 62, 64 extending from the two first corners 58, 60, respectively, intersect one another at a point 66 outside the perimeter 46 of the appliance 10. The first line 62 is parallel to a long side 68 of the first open area 50 and the second line 64 is parallel to a long side 70 of the second open area 50.

A third line 72 extends from the first corner 58 at an acute angle to the first line 62. The third line 72 extends to a first point 74 on the perimeter 46 so as to create the shortest distance between the first corner 58 and the perimeter 46 compared to all other points on the perimeter 46.

A fourth line 76 extends from the second corner 60 at an acute angle to the second line 64. The fourth line 76 extends to a second point 78 on the perimeter 46 so at to create the shortest distance between the second corner 60 and the perimeter 46 compared to all other points on the perimeter 46.

The length of the third and the fourth lines 72, 76 may be approximately 6 mm to approximately 13 mm. It can be appreciated, however, that the lengths of the lines 72, 76 can be less than or greater than the above range depending on the size of the appliance 10, the size of the open area(s) 50, 52 and the positioning of the open area(s) 50, 52 with respect to the perimeter 46.

FIG. 1A shows the open areas 50, 52 are positioned at angles 80, 82, respectively. The positioning angles 80, 82 are determined relative to two reference lines. A first reference line 84 passes through the first and second points 74, 78. A second reference line 86 is shifted a perpendicular distance below the first reference line 84; the second reference line 86 is parallel to the first reference line 84.

The second reference line 86 is at a distance of approximately 15-25 mm from the first and second points 74, 78. In one embodiment, the second reference line 86 is approximately 20 mm from the first and second points 74, 78. The distance the second reference line 86 is from the points 74, 78 may depend on the length of the long sides 68, 70 of the open areas 50, 52.

The angle 80, 82 that the open areas 50, 52 make with the second reference line 86 can vary, but in a preferred embodiment would range from 30 to 55 degrees. In most embodiments, the angle 80, 82 is an acute angle.

The preferred rectangular shape of the open areas 50, 52 was experimentally found to prevent forces from transmitting through appliance 10 to the underlying central incisor teeth 22 when loaded with a laryngoscope. Under load, the appliance 10 can deform along the sides (the long and/or short sides) of the open areas 50, 52, thereby changing the relative amount of open versus solid area of the appliance 10. This deformation process dissipates some of the forces acting on the appliance 10.

The preferred shape of the open areas 50, 52 is a rectangular slot with a length of approximately 10 mm to 15 mm and a width of approximately 0.5 mm to 3 mm. Other shapes, sizes and dimensions than disclosed herein may be used as well. While it is preferred the open areas 50, 52 have the same size, shape and angle as one another, the open areas 50, 52 may have different size, shapes and/or angles with respect to one another.

Figure 1B:
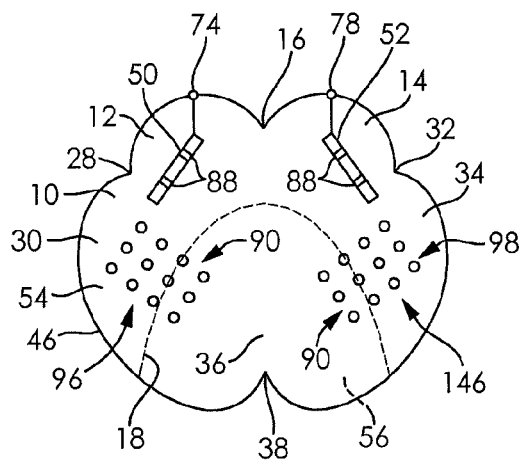
FIG. 1B is a top view of another embodiment of an appliance in a first, planar state.
Figure 2B:
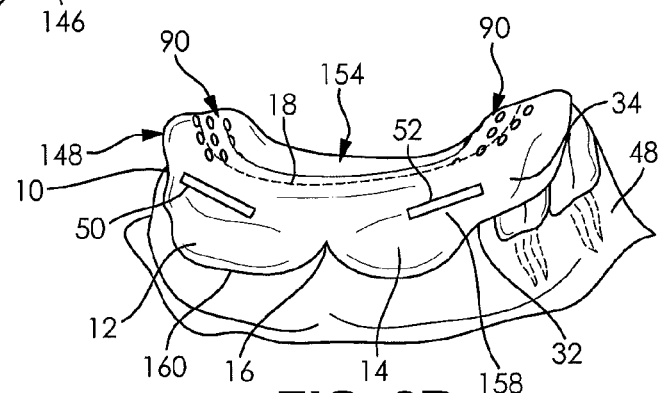
FIG. 2B is a front view of the appliance of FIG. 1 on the dentition of a patient.

Another embodiment with one or more reinforcing crossbars 88 dividing the rectangular open areas 50, 52 into smaller open areas is shown in FIG. 1B. In FIG. 1B, two crossbars 88 are located in each open area 50, 52. A greater number or fewer number of crossbars 88 may be used. In addition, while each open area 50, 52 is depicted as having the same number of crossbars 88, an equal number is not required. FIG. 1B depicts the crossbars 88 being equally spaced, and parallel, from one another but this is not required. In one embodiment, the crossbars 88 may be approximately 1-2 mm in width, but other widths are permissible. The first crossbar 88 in each open area 50, 52 may be approximately 3-3.5 mm from the first corners 58, 60, but other distances are also permissible.

The crossbars 88 prevent or reduce the open areas 50, 52 from becoming over-extended or stretched when the appliance 10 is fitted and/or when the appliance 10 is subject to deformation forces. More particularly, the crossbars 88 hold the sides of the open areas 50, 52 at a predetermined range of distances from one another during fitting and/or dissipation of appliance deformation forces.

The appliance 10 depicted in FIGS. 1A and 1B has a plurality of open spaces 90 on an inner portion 92 and an outer portion 94 of the bite line 18. The open spaces 90 extend through the appliance 10 from the first side 54 to the second side 56.

FIG. 1A depicts a first grid 96 and a second grid 98 both with circular open spaces 90. In FIG. 1A, the first and second grids 96, 98 comprise an equal number of rows and columns (4×4) with open spaces 90 having the same shape and spacing from one another. The grids 96, 98 may be divided in half by the bite line 18, but the grids 96, 98 may be divided in other proportions by the bite line 18, but the grids 96, 98 may be divided in other proportions by the bite line 18.

In the embodiment depicted in FIG. 1A, a first portion 100 of the grids 96, 98 extend inwardly into the rear palate portion 36 and a second portion 102 of the grids 96, 98 extend outward from the bite line 18. It is preferred that at a least a portion of a grid, or both grids 96, 98, are located over, or adjacent, the occluding surfaces 24 of the dentition when the appliance 10 is located in a patient's mouth. The grids 96, 98 assist in ensuring the appliance 10 conforms to the dentition since the open spaces 90 reduce rigidity and increase flexibility of the appliance material. The grids 96, 98 have other purposes as well, including force dissipation and absorption, as described below.

Figure 4A:
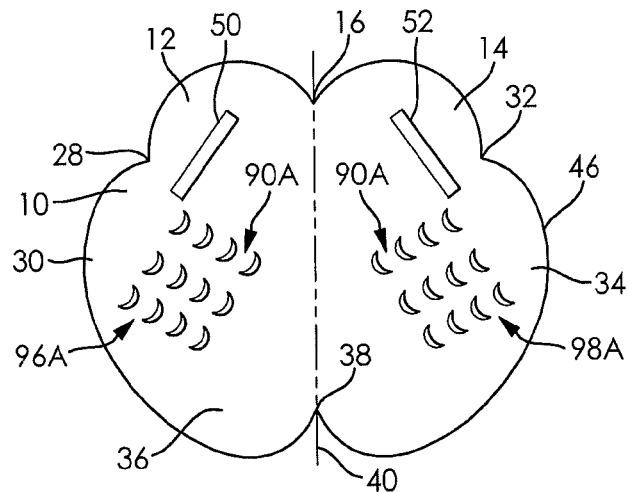
FIG. 4A is a top view of another embodiment of an appliance in a first, planar state.
Figure 4B:
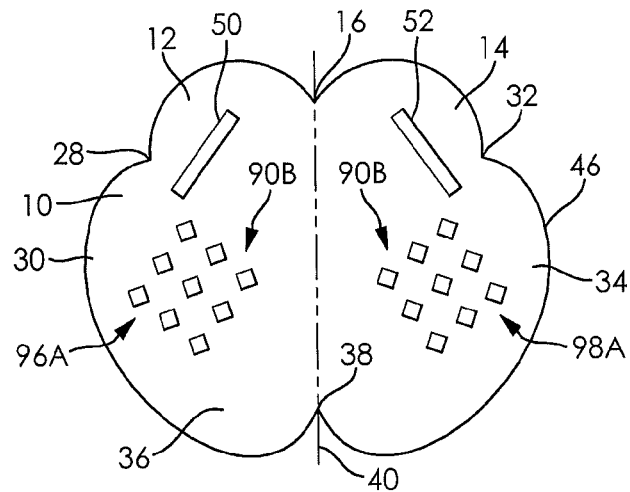
FIG. 4B is a top view of another embodiment of an appliance in a first, planar state.
Figure 4C:
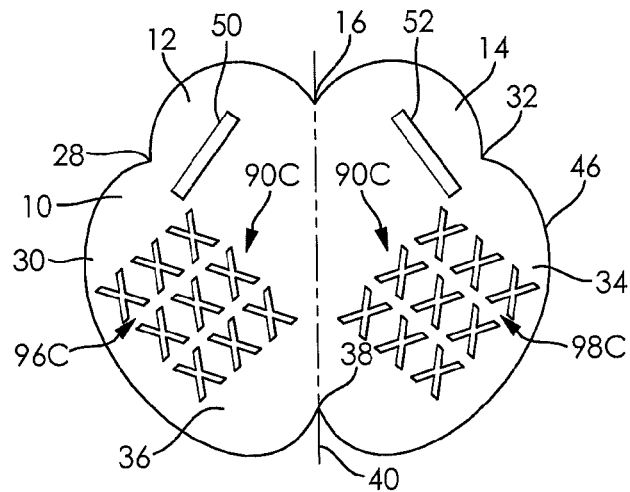
FIG. 4C is a top view of another embodiment of an appliance in a first, planar state.

While one embodiment of grids 96, 98 is shown in FIG. 4, grids of other shapes, sizes, locations and compositions of open spaces 90 are permissible. FIGS. 4A-4C depict alternative embodiments where some of the features from FIG. 1A also appear, but different grids are depicted.

FIG. 4A depicts an embodiment of a first grid 96A and a second grid 98A where the open spaces 90A of both grids 96A, 98A are crescent shaped and in a 4×3 pattern. The crescents open toward the perimeter 46 of the appliance 10.

FIG. 4B depicts another embodiment of a first grid 96B and a second grid 98B where the open spaces 90B of both grids 96AB, 98B are diamond shaped and arranged in a 3×3 pattern.

FIG. 4C depicts another embodiment of a first grid 96C and a second grid 98C where the open spaces 90C of both grids 96C, 98C are X-shaped and arranged in a 3×3 pattern.

In FIGS. 4A-4C, the open spaces 90A-90C are all in the same location as the open spaces 90 in FIG. 1A. It can be appreciated that the open spaces 90A-90C in these figures are not limited to just that location. Instead, the open spaces 90A-90C, regardless of their shape, can be located anywhere through the appliance 10. Further, while the open spaces 90A-90C in FIGS. 4A-4C are depicted in one orientation, they may be angled with respect to one another or one grid might be angled differently with respect to the other grid other than is shown.

FIGS. 4D-4F depict other embodiments where some of the features from FIG. 1 also appear. In addition to the FIG. 1 features, FIGS. 4D-4F have different open spaces.

In the embodiment depicted in FIG. 4D, a first group of open spaces 104 is located in the first and second front flaps 12, 14. The first group 104 may be located inboard of the perimeter 46 along the first and second front flaps 12, 14. At one end 106 of the first group 104, it may continue into the forward cusp area 108, as shown in FIG. 4D. At the other end 110 of the first group 104, it may terminate adjacent the side cusps 28, 32. While a first row of open spaces is shown in the first group 104, additional rows are permissible. The first group 104 is divided by the line of symmetry 40.

A second group 112 and a third group 114 may be located outboard of the bite line 18 and behind the open areas 50, 52. The second and third groups 112, 114 are located in the first and second side flaps 30, 34, respectively. The second and third groups 112, 114 may each have two rows with an equal number of open spaces 90. The second and third groups 112, 114 may be symmetrical about the line of symmetry 40.

A fourth group 116 is located inboard of the bite line 18 in the rear palate portion 36. The fourth group 116 may have a decreasing number of rows of open spaces 90 from the bite line 18 to the rear cusp 38.

FIG. 4E depicts yet another embodiment wherein a first group 118 of open spaces 90 is located outboard of the bite line 18 and a second group 120 of open spaces 90 is located inboard of the bite line 18. In the depicted embodiment, columns of open spaces 90 of the first group 118 and the second group 120 are aligned with one another.

The first group 118 may be comprised of one or more rows in whole or in part. As shown in FIG. 4E, the first group 118 has a first row 122 in a complimentary orientation to the bite line 18. A second 124 and third row 126 are depicted outboard of the first row 122. The second and third rows 124, 126 do not extend entirely along the first row 122, but stop adjacent the open areas 50, 52 and reside in the side flaps 30, 34.

The second group 120 is located inboard of the bite line 18 in the rear palate portion 36. The second group 120 comprises two rows of open spaces 90. The row 128 adjacent the bite line 18 has more open spaces 90 than the next inboard row 130. The groups 119, 120 are symmetrical about the line of symmetry 40.

FIG. 4F depicts another embodiment. In this embodiment, open spaces 90 have a generally oval shape. A first group 132 of open spaces 90 is located in the first and second front flaps 30, 34. The first group 132 may be located inboard of the perimeter 46 along the first and second front flaps 12, 14. The first group 132 may continue into the forward cusp area 108, as shown in FIG. 4F. The first group 132 may terminate at, or before, the side cusps 28, 32. While a first row of open spaces 90 is shown for the first group 132, additional rows are permissible.

A second group 136 and a third group 138 may be located behind the open areas 50, 52 in the side flaps 30, 34. The second and third groups 136, 138 may extend across the bite line 18 from the side flaps 30, 34 and into the rear palate position 36. The number of open spaces 90 in the rows and columns of the second and third groups 136, 138 may vary, as shown in FIG. 4F.

The columns of open spaces 90 in the second and third groups 136, 138 may be aligned across the bite line 18.

A fourth group 140 of open spaces 90 may be located in the rear palate portion 36. In the depicted embodiment, the fourth group 140 has an upside-down Y-shape with some open spaces 90 aligned with the rear cusp 38 and others on either side of the rear cusp 38.

In FIGS. 1 and 4A-F, the open areas 50, 52 are depicted as larger than the open spaces 90. More particularly, the open areas 50, 52 in these figures are longer in length than the open spaces 90. As can be appreciated by FIG. 4F, the open areas 50, 52 and spaces 90 can share the same type of shape, but as can be appreciated by the other figures, the open areas 50, 52 and spaces 90 can be different shapes.

The figures in the application depict certain embodiments of the open areas 50, 52 and spaces 90. It can be appreciated that other shapes, numbers, designs and/or orientations are permissible. It is preferred that regardless of the open areas 50, 52 and open spaces 90 selected, that the design selected is symmetrical about the line symmetry 40, but it is not required.

Figure 5A:
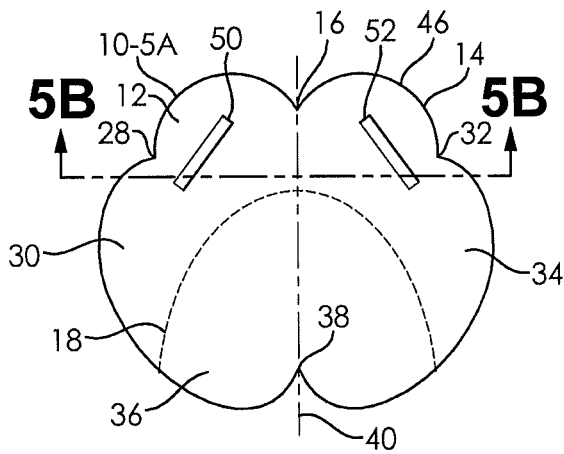
FIG. 5A is a top view of another embodiment of an appliance in a first, planar state.
Figure 5B:
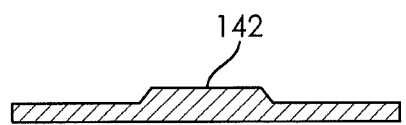
FIG. 5B is a side view along line 5B-5B of FIG. 5A.

FIGS. 5A-B depict an embodiment that has the same features as FIG. 1A, but the thickness of the appliance 10 is not constant as it is in FIG. 1A. More particularly, as best seen in FIG. 5B, the thickness of the appliance 10-5A increases between the two open areas 50, 52 in the region of the bite line 18 in order to reinforce the area where the highest loads may be experienced, while keeping the rest of the appliance 10-5A sufficiently thin so as to not obstruct the entry pathway into the larynx. The area of increased thickness 142 may extend rearward in a continuous fashion from the forward cusp 16 to at least parallel to the open areas 50, 52. The area 142 may extend rearward beyond the open areas 50, 52 as well, such as beyond the bite line 18 and into the rear palate portion 36. The total increase in thickness of area 142 should be sufficient to add additional dental protection for the given circumstance but not exceed a value that will obstruct, hinder, or clutter the entry pathway to the larynx.

The area of increased thickness 142 is preferably at least where the two central incisors 22 are located. As mentioned above, forces during a transoral procedure are often applied to the central incisors 22 placing these teeth at the greatest risk for damage and/or injury. The increased thickness in the appliance at the bite line 18 relative to the uniform thickness of the remainder of the oral appliance functions to provide additional capability to reduce and/or dissipate forces applied to the dentition in this region which might be at an even greater risk for damage or injury than during a typical transoral procedure by way of the specific nature of the instrument in use or the type of procedure underway.

The area of increased thickness 142 in FIG. 5B may transition from the original thickness of the sheet abruptly (e.g., a 90 degree angle) or in a ramp-like manner as shown in FIG. 5B. The area of increased thickness 142 is unitary, one-piece and integrally formed with the rest of the appliance 10-5A.

Figure 6A:
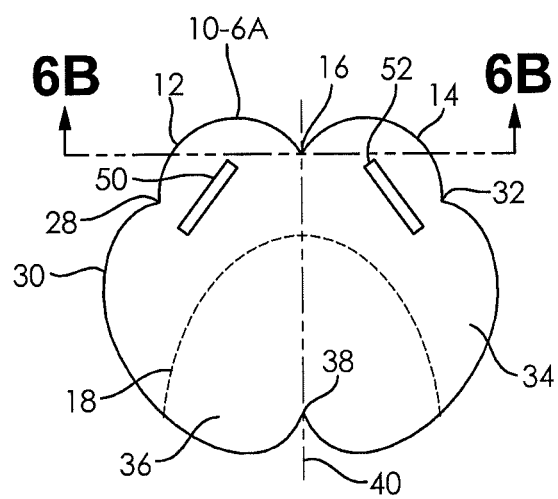
FIG. 6A is a top view of another embodiment of an appliance in a first, planar state.
Figure 6B:
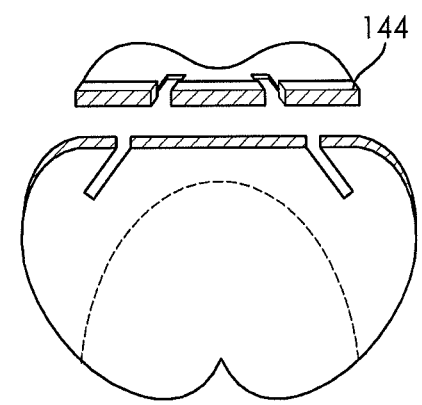
FIG. 6B is a side view along line 6B-6B of FIG. 6A.

FIGS. 6A-6B depict an embodiment that has the same features as FIG. 1A, but the thickness of the appliance 10-6A is not constant as it is in FIG. 1. More particularly, as best seen in FIG. 6B, the thickness of the first and second front flaps 12, 14 is increased compared to the rest of the appliance 10-6A. Unlike the embodiment in FIG. 5B that only increases the thickness between the open areas 50, 52, the embodiment of FIG. 6B shows an area of increased thickness 144 across the appliance 10-6A from one side cusp 28 to another side cusp 32.

The total increase in thickness of area 144 should be sufficient to add additional dental protection for the given circumstance but not exceed a value that will obstruct, hinder, or clutter the entry pathway to the larynx. The area of increased thickness 144 may extend continuously from the front flaps 12, 14 rearwardly to at least the open areas 50, 52. As shown in FIG. 6B, the area of increased thickness 144 extends to the open areas 50, 52; the area of increased thickness 144 may extend to the bite line 18 or beyond into the rear palate portion 36. The increased thickness in the appliance relative to the uniform thickness of the remainder of the oral appliance functions to provide additional capability to reduce and/or dissipate forces applied to the dentition in this region which might be at an even greater risk for damage or injury than during a typical transoral procedure by way of the specific nature of the instrument in use or the type of procedure underway.

The embodiments in FIGS. 5A-B and 6A-6B are contemplated to be used in situations where high forces are anticipated. The increased thickness of the appliance advantageously dissipates the additional forces but care must be taken so as not to thicken the appliance so much that is prevents full visualization of the voice box and trachea.

A method of using the dental appliances described above to protect the dentition of a patient during a transoral procedure follows. The following description will use the embodiment of FIG. 1A, but it can be appreciated that the method is readily used with the other embodiments.

The appliance 10 is initially in a first planar state 146. At room temperature, the appliance 10 is rigid. The appliance 10 may be heated such as by convection, conduction and/or radiation until it is pliable. Once pliable, the appliance 10 is located adjacent the dentition of a patient. In the preferred embodiment, the appliance 10 is located adjacent the maxilla (upper dentations) into a second, non-planar state 148 described below, and depicted in FIG. 2A. Alternatively, the appliance 10 may be located adjacent the mandible (lower jaw), or a first sheet can be located adjacent the maxilla and a second sheet can be located adjacent the mandible.

Continuing with the embodiment wherein the appliance 10 is located just adjacent the maxilla, the crowns of the dentition 20, 24 are positioned adjacent the bite line 18 on the appliance 10. The appliance 10 is moved into contact with the dentition 20, 24 and then molded around the dentition 20, 24. More particularly, the first and second front flaps 12, 14 are molded in front of the outward facing surfaces 150 of the dentition. Similarly, the side flaps 30, 34 are molded in front of the outward facing surface 150 of the dentition. Preferably, the first and second front flaps 12, 14, and also the side flaps 30, 34, are located vertically, or with a slight angle variance from vertical (e.g. 10 degrees), from the bite line 18. The flaps 12, 14, 30, 34 are preferably located in this orientation because it minimizes the mobility of the central incisor teeth 22 when the tips of these teeth 22 are pressure loaded.

The rear palate portion 36 is molded upwardly into contact with the hard palate 152 so that it assumes a complementary shape thereto. More particularly, the rear palate portion 36 is molded into an upstanding arch-shaped 154 form complementary to the shape and size of the patient's hard palate 152. The arch 154 extends upwardly with respect to the bite line 18. Any portion of the rear palate portion 36 that contacts the palate 152 of the patient should be free of structures that could irritate or damage the palate 152, such as rough corners and/or sharp edges or transitions.

The rear palate portion 36 acts as an anchor reducing or preventing the possibility that the appliance will become dislodged from the dentition. More particularly, when the incisor teeth are pressure loaded, the rear palate portion 36 provides a counter force by virtue of its support at least against the patient's hard palate.

The upward location of the flaps 12, 14, 30, 34 and the rear palate portion 36 effectively encases the outward and rear surfaces 150, 152 of the maxilla dentition in a channel 158, which can be appreciated in FIGS. 2A-D. The channel 158 protects the forward and rear surfaces of many of the patient's teeth from contact with medical devices and tools.

When the appliance 10 is fit onto the dentition of a patient, the forward cusp 16 falls centrally between the two maxillary central incisor teeth 22. The rear cusp 38 is aligned with the forward cusp 16 along the line of symmetry 40.

The first and second forward flaps 12, 14 cross over a maxillary teeth-gum intersection line 160 and extend over the soft gum tissue 48. During experiments, it was found that first and second forward flaps 12, 14 that extend beyond the maxillary teeth-gum intersection line 160 effectively prevented the central incisor teeth 22 from moving during high pressure loading. In one embodiment, the flaps 12, 14 extend beyond the teeth-gum intersection line 160 approximately 0.25 to 0.35 mm. While one range of extension is mentioned above, it can be appreciated that this dimension can be larger or smaller to cover more or less of the soft gum tissue 48.

In addition to manually locating the appliance 10 in position as described above, the patient can draw air through the open spaces 90 and/or through the open areas 50, 52. The vacuum created by the patient by drawing the air through the spaces 90 and/or through the open areas 50, 52 pulls the pliable appliance 10 into conformal contact with the dentition.

The manual manipulation and/or the vacuum applied to the appliance 10 causes an interior surface 162 of the appliance 10 to mold into intimate contact with the dentition. As the appliance 10 cools, it may shrink into further contact with the dentition. During cooling, the appliance 10 hardens into a shape that well adheres to the contours of every unique tooth. This adherence ensures the appliance 10 does not become dislodged during transoral procedures. In addition, the adherence and thin dimension of the appliance 10 provides a clear, unobstructed view of the patient's voice box and trachea.

The open areas 50, 52 and open spaces 90 in the appliance 10 provide a conformal fit of the appliance 10 onto any dentition and enable a secure custom fit by changing in size and in shape in all or some when the appliance 10 is in the pliable condition. The secure, custom fits enables the appliance to remain fixed on the dentition. An embodiment of the dental appliance 10 without open areas 50, 52 and/or open spaces 90 is envisioned though it may not result in a conformal and secure fitting compared to when the spaces 90 and/or areas 50, 52 are present. The open spaces 90 and areas 50, 52 allow the softened thermo-polymer material to be formed into a three-dimensional shape without buckling, bunching, creasing, or bulging.

If the appliance 10 has to be re-fitted after it has cooled and hardened, it can be warmed to its softening point and the fitting process can be repeated because its second state is only a semi-permanent state.

With the appliance 10 in place, forces applied to the dentition during a transoral procedure through the appliance 10 are reduced and dissipated. For example, if forces are applied to the maxillary central incisor teeth 22 that attempt to push them forward during an intubation procedure (a 25 N force is applied to the maxillary central incisor teeth is typical during such a procedure), the appliance 10 will resist those forces and prevent the teeth 22 from shifting forward.

The ability of the appliance 10 to dissipate forces can be appreciated from the following exemplary data. When a load of 42.8 Newtons (N) was applied to the outside of the appliance 10 adjacent the maxillary central incisor teeth 22, the appliance 10 was able to dissipate 74% of that load, and the maxillary central incisor teeth 22 only experienced a transmitted load of 11.0 N. When the applied load was slightly increased to 48.1 N, the appliance 10 was able to dissipate 76% of the load; the same dentition 22 experienced a transmitted load of only 11.4 N.

When the applied load was further increased to 70.2 N, the appliance 10 dissipated an even greater percentage of the applied load. Despite an increase in the applied load of approximately a third, the appliance 10 only allowed the underlying dentition to experience an 8 N load thus dissipating 88.3% of the applied load. This significant augmentation in the percentage of load force dissipated is attributed to the fact that the higher applied load caused some of the appliance 10 to undergo plastic deformation thereby enabling an additional mechanism to dissipate a portion of the applied load. In other words, in the range of the above-mentioned applied loads, the appliance 10 was able to dissipate a greater percentage of the applied load as the applied load increased.

Next, a much higher force load of 107.9 N was applied to the appliance 10. The appliance 10 still dissipated 79.8% of this very high applied load allowing the underlying dentition 22 to experience a transmitted load of only 21.8 N.

In addition to, or separate from plastic deformation, the appliance 10 material surrounding the open spaces 90 and open areas 50, 52 undergoes elastic deformation to dissipate forces. More particularly, the boundaries of the open spaces 90 and open areas 50, 52 deform (e.g., expand, contract, twist) in whole or in part to absorb and redirect forces applied to the appliance 10 through the appliance 10 rather than transmit the forces to the underlying dentition.

Figure 7A:
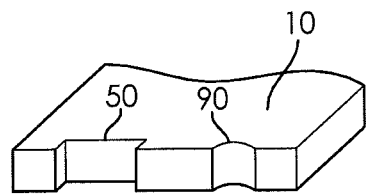
FIG. 7A is a partial cross-sectional side view of an open space and open area of the appliance.

FIG. 7A depicts a cross section through an open space 90 and one of the open areas (50 in this case) of an appliance 10. FIG. 7A depicts the open space 90 and the open area 50 in the condition where no force is applied so the space 90 and area 50 are not deformed.

Figure 7B:
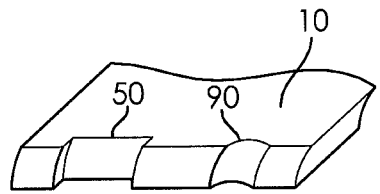
FIG. 7B is a partial cross-sectional side view of the open space and the open area of the appliance of FIG. 7A subject to a force.

FIG. 7B depicts the same open space 90 and open area 50 subject to a force. The force deforms the open space and/or the open area 50 resulting in dissipation of the force.

In FIG. 7B, the open space 90 is deformed as a result of one kind of force from a circular cross-section to an oval cross-section. The open area 50 is deformed from a rectangular cross-section to an oval cross-section. The shape change of the open space 90 and/or open area 50 expends some or all of the energy of the force traveling through the appliance 10.

In one example, because the appliance 10 maintains a constant volume, when a force encounters an open space 90 or open area 50, the deformed open space 90 and/or open area 50 compresses the adjacent open spaces 90 and/or open areas 50. The combination of deformation and compression of the open spaces 90 and/or open areas 50 results in force dissipation.

One kind of force, such as caused by a shearing action, may travel through the appliance 10 in a wave or waves. The waves may travel along an outer surface of the appliance 10 and/or through the appliance 10.

Another kind of force is a force that is normal to the appliance 10. The normal force can be applied substantially at once, it can be repeated, and/or it can increase or decrease in intensity.

While FIG. 7B depicts the open space 90 and the open area 50 both deformed to dissipate a force, it can be appreciated that only one or the other might be deformed. Further, while FIG. 7B depicts the open space 90 and the open area 50 deformed into oval cross-sections, they may be deformed into other shapes and/or the shapes of the deformed open space 90 do not have to match the shape of the deformed open area 50.

The open spaces 90 and/or the open areas 50 are located in the appliance 10 to maximize tensile strength of the appliance 10 without exposing any of the protected dental surfaces to the unprotected teeth on the opposite jaw. The locations of the open spaces 90 and the open areas 50 also optimize saliva flow around the dentitions, which improves comfort. More particularly, saliva can be sucked through the open spaces 90 and/or open areas 50.

The open spaces 90 and the open areas 50 also function to improve breathing by allowing the guard to be thinner and thus take up less space in the mouth.

Based on the foregoing, it can be appreciated that the appliance material, the location of that material on the patient's dentition and palate as described herein, the open spaces, the open areas, and/or plastic and/or elastic deformation effectively diminishes forces transmitted in the axial (normal) direction, as well as in the horizontal direction, with respect to the dental surfaces.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A dentition protecting guard for transoral medical procedures, comprising:
    an outer perimeter defined by two front flaps separated by a forward cusp, and two side flaps separated from said front flaps by side cusps;
    a single, rectangular, force dissipating open area in each of said front flaps, wherein each open area has a leading portion angled toward an appliance line of symmetry and a trailing portion angled away from said line of symmetry;
    wherein a first line parallel a long side of a first of said rectangular open areas intersects with a second line parallel a long side of a second of said rectangular open areas outside of said outer perimeter,
    wherein said first line and said second line intersect with said line of symmetry outside of said outer perimeter;
    a symmetric, arch-shaped bite line area extending through said line of symmetry said bite line area only located behind said open areas;
    a first side of said bite line area extending through a first set of circular, force dissipating open spaces and a second side of said bite line area extending through a second set of circular, force dissipating open spaces; and
    an arch-shaped rear palate portion continuously extending from said first set of circular open spaces to said second set of circular open spaces;
    wherein said line of symmetry extends from said forward cusp to a rear cusp in said rear palate portion, wherein said forward cusp and said rear cusp extend inwardly into said intubation guard the same amount.

2. The guard of claim 1, wherein said two front flaps extend over a maxillary teeth-gum intersection and over soft gum tissue.

3. The guard of claim 1, wherein said outer perimeter is curvilinear including said front flaps and said side flaps.

4. The guard of claim 1, wherein each of said open areas is located at an angle with respect to a first reference line extending through outermost points on each of said front flaps and a second reference line extending through said rear palate portion parallel to said first reference line.

5. The guard of claim 4, wherein said angle said open areas make with said second reference line is approximately 30 to 55 degrees.

6. The guard of claim 1, wherein said open areas have a greater length than width.

7. The guard of claim 1, wherein said rear palate portion is located behind said bite line area.

8. The guard of claim 1, wherein said first set of open spaces and said second set of open spaces are separated from one another by said rear palate portion.

9. The guard of claim 1, wherein said front flaps, said side flaps, said bite line area and said rear palate portion have uniform thickness.

10. The guard of claim 1, wherein said front flaps have a greater thickness than said bite line area and said rear palate portion.

11. A dentition protecting guard for transoral medical procedures, comprising:
a flat sheet of thermopolymer material having a first planar side, a second planar side and a perimeter defining a first cusp and a second cusp, said cusps define a line of symmetry for said sheet extending from said first cusp to said second cusp, wherein said forward cusp and said rear cusp extend inwardly into said intubation guard the same amount;
an area for receiving crowns of dentition that extends across said line of symmetry;
wherein said first and second planar sides and said perimeter define two front flaps and two side flaps;
a single, rectangular, force dissipating open area in each of said front flaps extending through said sheet, said open areas having lengths greater than their widths,
wherein a first line parallel a long side of a first of said rectangular open areas intersects with a second line parallel a long side of a second of said rectangular open areas outside of said outer perimeter,
wherein said first line and said second line intersect with said line of symmetry outside of said outer perimeter;
a plurality of circular, force dissipating open spaces extending through said sheet and arranged adjacent a bite line area behind said open areas; and
a rear palate portion inboard of said bite line area, said second cusp located in said rear palate portion.

12. A method of protecting the dentition of a patient during a transoral procedure or intubation, comprising:
providing an appliance guard in a planar first state having two front flaps, two side flaps, an arch shaped bite line area, and a rear palate portion;
locating the crowns of the dentition of a patient in contact with said bite line;
molding said appliance guard into a second non-planar state to the palate of said patient and also about at least forward surfaces and rear surfaces of maxillary dentition of the patient;
dissipating a force applied to said maxillary dentition through said appliance with a single, rectangular slot in said first front flap and/or a single, rectangular slot in said second front flap,
wherein said force is dissipated through a temporary deformation of said slot in said first front flap and/or said second slot in said second front flap from a first shape to a second shape,
wherein a first line parallel a long side of said single rectangular slot in said first front flap intersects with a second line parallel a long side of said single rectangular slot in said second front flap outside of said outer perimeter,
wherein said first line and said second line intersect with said line of symmetry outside of said outer perimeter;
wherein said rear palate portion counters said force through its support against a patient's hard palate.

13. The method of claim 12, wherein said appliance guard is put into said second non-planar state by warming the appliance and by manually manipulating the appliance about said dentition.

14. The method of claim 13, wherein said appliance is put into said second non-planar state by said patient drawing air through a plurality of open spaces in said appliance and said first slot and said second slot.

15. The method of claim 13, wherein said appliance is put into said second non-planar state by letting said appliance cool, shrink and harden into intimate contact with the dentition of the patient.

16. The method of claim 12, wherein said force is dissipated by extending a first front flap and a second front flap beyond a dentition-gum intersection line.

17. The method of claim 12, wherein said force is dissipated through a temporary deformation of a said plurality of open spaces in said appliance.

18. The method of claim 12, wherein said force is dissipated through elastic deformation of said appliance.

19. The method of claim 12, wherein said force is dissipated through plastic deformation of said appliance.

20. The method of claim 12, wherein said first slot, said second slot and/or said plurality of open spaces shift shapes while said intubation guard is molded.

21. The method of claim 12, wherein said rear palate portion located inward of said bite line area and comprised of a rear cusp that extends inwardly into said rear palate portion, said rear cusp being aligned with a forward cusp.

22. The method of claim 21, wherein said rear palate portion extends continuously from one leg of said arch-shaped bite line to another leg of said arch-shaped bite line.

23. A dentiton protecting guard for transoral medical procedures, comprising:
a flat sheet having a first planar side and a second planar side parallel to said first planar side;
a perimeter bounding said two sides and defining at least two cusps that extend inwardly into said flat sheet;
a continuous palate portion within said perimeter, said palate portion having a plurality of open spaces extending from said first side to said second side; and
only two rectangular, force dissipating open areas extending from said first side to said second side outside of said palate portion;
wherein a first line parallel a long side of a first of said rectangular open areas intersects with a second line parallel a long side of a second of said rectangular open areas outside of said outer perimeter;
wherein a line of symmetry for said guard extends from a forward cusp to a rear cusp in said palate portion, wherein said forward cusp and said rear cusp extend inwardly into said intubation guard the same amount,
wherein said first line and said second line intersect with said line of symmetry outside of said outer perimeter.

* * * * *